United States Patent [19]

Silverstein et al.

[11] Patent Number: 4,646,722

[45] Date of Patent: Mar. 3, 1987

[54] PROTECTIVE ENDOSCOPE SHEATH AND METHOD OF INSTALLING SAME

[75] Inventors: Fred E. Silverstein; Eric A. Opie, both of Seattle, Wash.

[73] Assignee: Opielab, Inc., Seattle, Wash.

[21] Appl. No.: 680,068

[22] Filed: Dec. 10, 1984

[51] Int. Cl.[4] .............................................. A61B 1/00
[52] U.S. Cl. ...................................................... 128/4
[58] Field of Search ................... 128/4, 6, 7, 5, 3, 23

[56] References Cited

U.S. PATENT DOCUMENTS

| | | | |
|---|---|---|---|
| 2,922,415 | 1/1960 | Campagna | 128/4 |
| 3,144,020 | 8/1964 | Zingale | 128/4 |
| 3,162,190 | 12/1964 | Del Gizzo | 128/6 |
| 3,794,091 | 2/1974 | Ersek et al. | 128/23 X |
| 3,809,072 | 5/1974 | Ersek et al. | 128/23 |
| 3,866,601 | 2/1975 | Russell | 128/4 |
| 3,980,078 | 9/1976 | Tominaga | 128/4 |
| 4,076,018 | 2/1978 | Heckele | 128/6 |
| 4,085,742 | 4/1978 | Okada | 128/4 |
| 4,132,227 | 1/1979 | Ibe | 128/4 |
| 4,201,199 | 5/1980 | Smith | 128/7 |
| 4,248,214 | 2/1981 | Hannah et al. | 128/7 |
| 4,254,762 | 3/1981 | Yoon | 128/4 |
| 4,327,735 | 5/1982 | Hampson | 128/DIG. 9 X |
| 4,329,995 | 5/1982 | Anthracite | 128/4 X |

FOREIGN PATENT DOCUMENTS 1405025  9/1975  United Kingdom .

*Primary Examiner*—William H. Grieb
*Attorney, Agent, or Firm*—Seed and Berry

[57] ABSTRACT

An endoscope sheath having a flexible tube surrounding the elongated core of an endoscope. The flexible tube has a transparent window near its distal end positioned in front of the viewing window of the endoscope. Channels for taking biopsies, injecting air or injecting water to wash the window of the sheath may extend along the endoscope, either inside or outside the sheath. Where the channels are positioned inside the sheath, they may be inserted in a longitudinal groove formed in the endoscope core. The protective sheath may be used with either end-viewing endoscopes or side-viewing endoscopes. In the latter case, the channel for taking biopsies extends through an elongated elastomeric membrane so that a catheter through the biopsy channel may be moved longitudinally by manipulation of an elevator. The protective sheath may be installed by rolling the elastomeric tube into an annular configuration and then unrolling the tube over the core of the endoscope. Alternatively, the tube may be inflated in its unrolled configuration to expand the tube and allow it to be easily slipped onto the endoscope core. A variety of specialized endoscopes may be created by using protective sheaths having a variety of special purpose medical instruments mounted at the end of a biopsy channel and operated through the channel.

31 Claims, 11 Drawing Figures

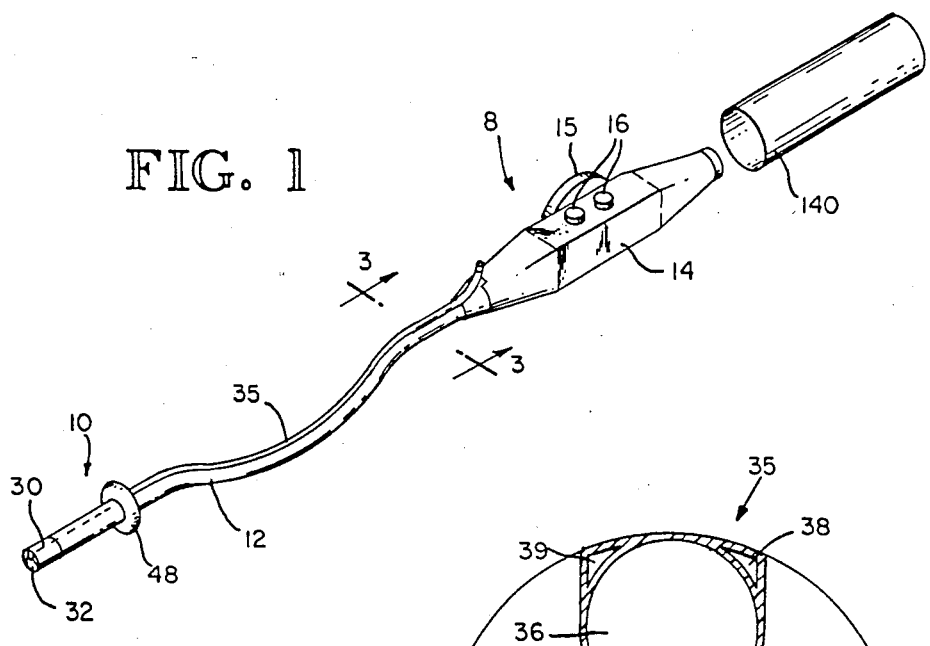
FIG. 1
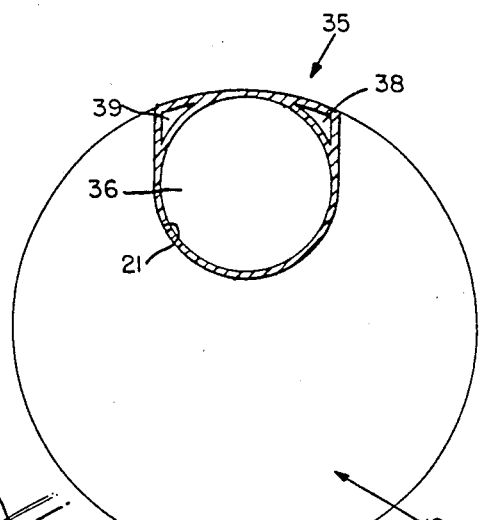
FIG. 3
FIG. 2
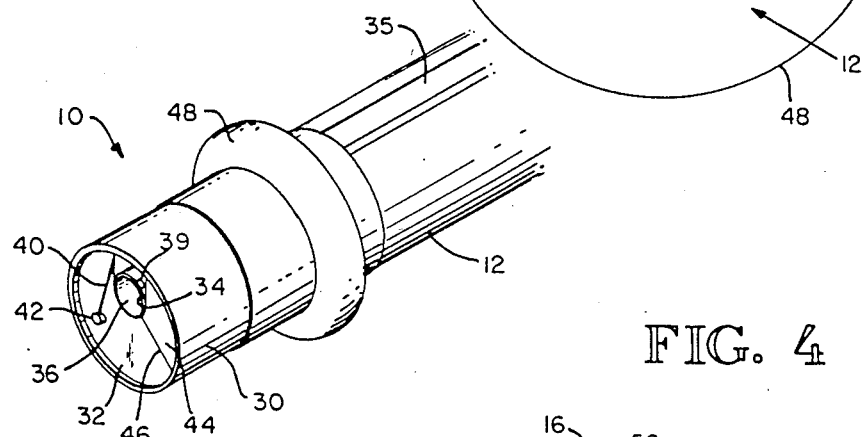
FIG. 4
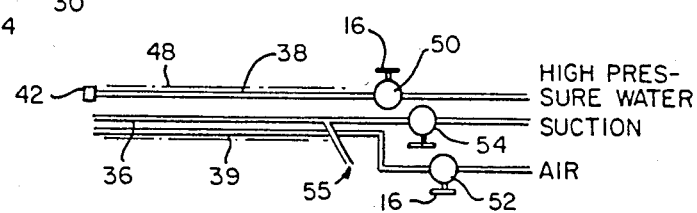

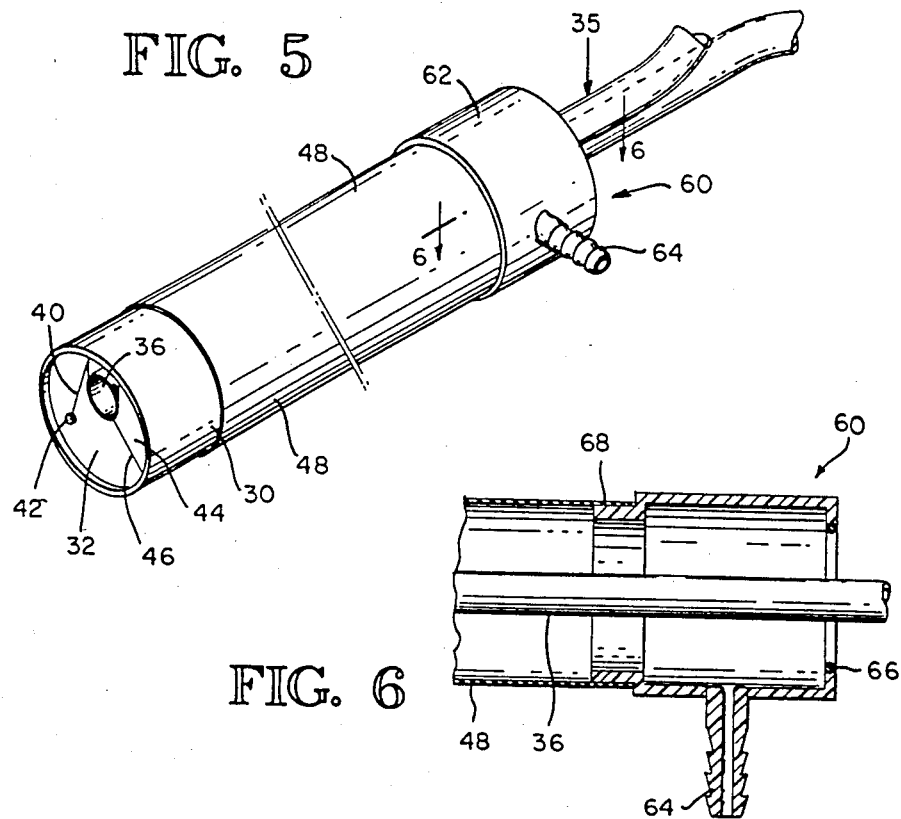
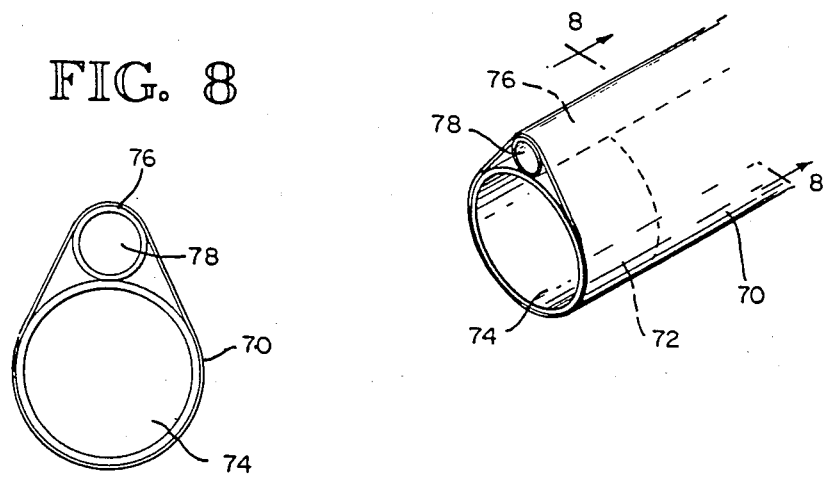

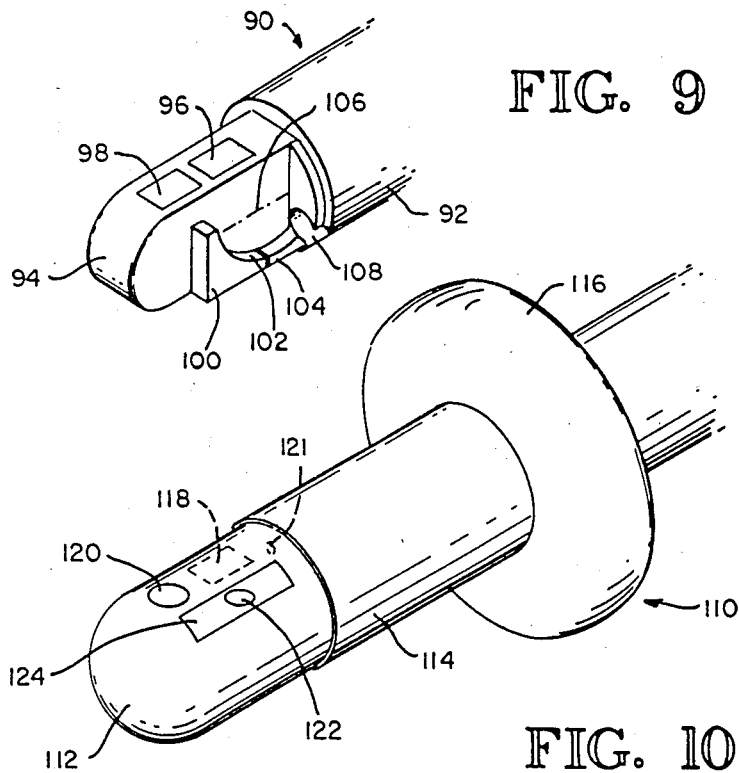
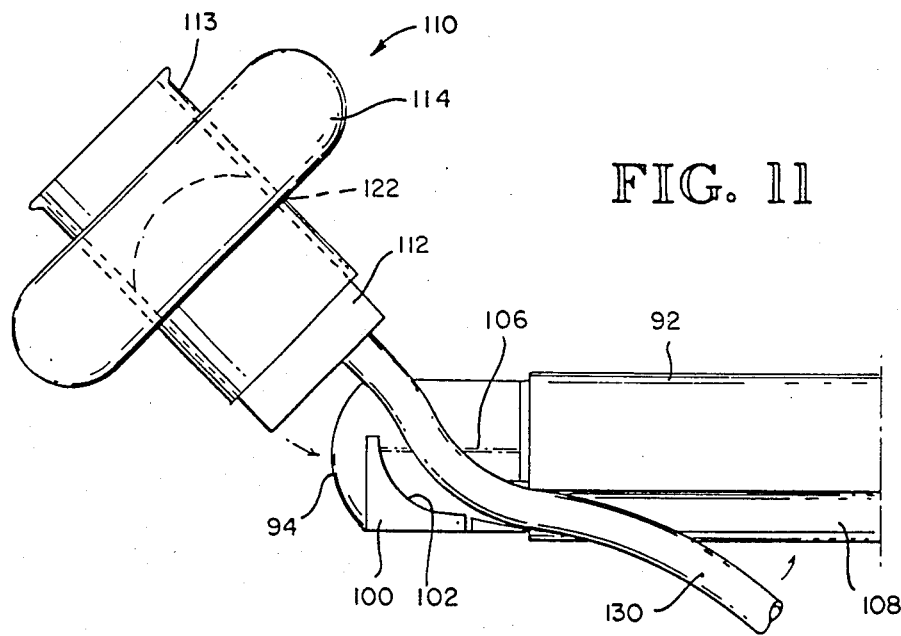

PROTECTIVE ENDOSCOPE SHEATH AND METHOD OF INSTALLING SAME

TECHNICAL FIELD

This invention relates to the field of endoscopy, and more particularly, to a device for inexpensively isolating and endoscope from virus and bacteria, and for allowing a variety of specialized endoscope instruments to be implemented from a single basic endoscope core.

BACKGROUND ART

The use of endoscopes for diagnostic and therapeutic indications is rapidly expanding. To improve performance, endoscopes have been optimized to best accomplish their purpose. Therefore, there are upper endoscopes for examination of the esophagus, stomach and duodenum, colonoscopes for examining the colon, angioscopes for examining blood vessels, bronchoscopes for examining the bronchi, laparoscopes for examining the peritoneal cavity, and arthroscopes for examining joint spaces. The discussion which follows will apply to all of these types of endoscopes. Instruments to examine the rectum and sigmoid colon, know as flexible sigmoidoscopes, are good examples of the usefulness of this technology. These devices are expensive, used in a contaminated environment for a procedure which is brief (5-10 minutes) and where problems of cleaning time and contamination are important factors. There has been a large increase in the use of the "flexible sigmoidoscope" for use in screening symptomatic and asymptomatic patients for colon and rectal cancer. Ideally, flexible sigmoidoscopes must be used rapidly and inexpensively in order to maintain the cost of such screening at acceptable levels. Typically, a clinic would like to perform five to ten sigmoidoscope examinations each hour. One significant problem with making such examinations quick and inexpensive is the time necessary for adequately cleaning the device.

Although endoscopes can be cleaned in about two to four minutes, this relatively cursory cleaning may not be adequate for complete disinfection or sterilization. Even a more complete cleaning requiring on the order of eight to ten minutes may not allow adequate cleaning, particularly in view of the increasing problems with contagious viruses. Even with the use of chemicals such as gluteraldehyde, adequate cleanliness may not be possible.

While the external surfaces of endoscopes can often be adequately cleaned, endoscopes typically have air, water, biopsy and suction channels extending along their lengths which come into contact with body tissues or fluids. It is extremely difficult to adequately clean these channels even when skilled health practitioners spend a great deal of time on the cleaning procedure.

Even if endoscopes can be adequately cleaned in eight to ten minutes, the cleaning still prevents endoscopy examinations from being relatively inexpensive. While a physician may spend five to ten minutes performing the endoscopy, he or she will generally waste a great deal of time waiting for the endoscope to be cleaned before he or she can conduct another endoscopy. A partial solution to the "idle time" problem is to purchase multiple instruments so one can be used as the others are being cleaned. However, the expense of having duplicate endoscopes of each type makes this solution impractical especially for physicians' offices and smaller clinics.

Not only must the idle time of the physician be added to the cost of endoscopic examinations, but the time spent by a nurse or other hospital personnel in the cleaning as well as the cost of disinfecting chemicals must also be added to the cost of the examination. Although washing machines are available to clean endoscopes, these machines are expensive and not significantly faster than washing by hand. As a result, with conventional endoscopic procedures, both the physician and the relatively expensive endoscope have a downtime approaching fifty percent.

Another problem with cleaning endoscopes by hand or with a washing machine is that the chemicals used are toxic and potentially injurious to the staff who use them, and the environment into which they are discharged. To use some of these chemicals safely, such as gluteraldehyde, requires a dedicated ventilated hood, which uses up space and is expensive to install and operate. The chemicals are also potentially toxic to the patient in that if residue remains after cleaning and rinsing the instrument, the patient could have a reaction to the chemicals. A limitation to this approach is that some types of chemicals may damage the outer surfaces of endoscopes after a number of washings.

In short, conventional endoscope cleaning techniques greatly increase the cost of endoscopic procedures. Furthermore, while the risk of contamination using endoscopes is often far less than the risk of alternative procedures, such as surgery, there is nevertheless a risk that endoscopes are not adequately cleaned to prevent the risk of transmission of infectious diseases from one patient to the next.

In the health care field, the problems of contaminated instruments transmitting disease from one patient to the next have generally been solved by making such instruments disposable. However, this has not been thought possible in the field of endoscopy because endoscopes are very sophisticated, and hence, expensive instruments. Moreover, it has not been thought possible to isolate the endoscope from the patient or the external environment because the endoscope itself has channels inside it that are used as a conduit for body fluids and tissues, such as, for example, in taking biopsies. The only method currently available to actually sterilize an endoscope is to use gas sterilization with ethylene oxide gas. However, there are several significant disadvantages in using this procedure. The procedure is very slow; it takes 24 hours, during which the endoscope cannot be used. Also, the gas affects the the plastic of the endoscope and may limit the lifespan of the instrument. Finally, the gas is toxic, and, therefore, great care must be taken to ensure that no residue remains that might cause patient irritation during contact with the endoscope.

As a result of the above-described limitations in using and cleaning endoscopes by conventional techniques, there has not heretofore been an acceptable solution to the problem of making endoscopy procedures both inexpensive and entirely safe.

DISCLOSURE OF INVENTION

It is an object of the invention to provide an endoscope isolation device that is inexpensive, results in minimum downtime of the endoscope and physician, and which entirely prevents the transmission of disease from one patient to another.

It is another object of the invention to provide and endoscope sheath for isolating an endoscope from the patient and the external environment which can be rapidly applied and removed.

It is still another object of the invention to provide an endoscope sheath for isolating an endoscope from a patient and the external environment which does not interfere with the procedure or the operation of the endoscope.

It is a further object of the invention to provide an endoscope sheath that has disposable biopsy, suction, air and water channels, thus making it unnecessary to attempt cleaning these channels.

It is a further object of the invention to provide various configurations of sheaths that can be used with one central core endoscope, thereby providing a family of endoscope, each tailored to a specific use.

It is a further object of the invention to provide an endoscope sheath that may include channels dedicated to specific diagnostic and therapeutic purposes.

These and other objects of the invention are provided by an endoscope sheath in the form of a thin-walled, flexible, elongated tube fitting over and tightly surrounding an endoscope. The sheath has an opening at its proximal end for receiving the distal end of the endoscope and a window near its distal end that is positioned over the viewing window of the endoscope. As a result, the tube completely shields the endoscope from the patient and the external environment while permitting the patient to be viewed through the viewing window. The window of the sheath may face in either an axial direction to accommodate end-looking endoscopes, or in a radial direction to accommodate side-looking endoscopes.

In the event that a suction, biopsy, air or water channel is desired, a channel that can be integrally formed with the sheath extends along the length of the sheath. Alternatively, the disposable channel can be preloaded into the endoscope prior to covering the shaft of the endoscope with a sheath. In either case, the channel has open distal and proximal ends so that the interior of the channel is externally accessible but isolated from the interior of the sheath. The distal end of the channel preferably extends to a point near the viewing window of the endoscope. The channel may be positioned either along the exterior wall or along the interior wall inside the sheath and, in the event that the channel is positioned inside the sheath, the distal end of the channel extends through the distal end of the sheath. In order to accommodate the channel positioned within the sheath, the channel may be inserted within a longitudinal groove formed in the endoscope so that the channel is recessed within the periphery of the endoscope. The sheath may, of course, include multiple channels and the channel may perform a variety of functions. The channels are preferably inserted in respective longitudinal grooves formed in the endoscope. A washing nozzle may be mounted in the distal end of a channel, with the nozzle facing the exterior surface of the window of the sheath. As a result, water forced into this channel is sprayed onto the external surface of the window for cleaning purposes. Another channel is used to introduce gas (usually room air or $CO_2$) to distend the organ lumen. The window may be mounted in a relatively rigid, cylindrical support body connected to the distal end of the sheath in coaxial relationship with the endoscope.

The endoscope sheath may be installed on the endoscope with a variety of methods. The sheath may be rolled up along its length from its proximal end to its distal end. The distal end of the sheath is then placed in contact with the distal end of the endoscope and unrolled onto and along the length of the endoscope. Where the sheath has an internal channel extending along its length, the channel is placed in the longitudinal groove of the endoscope before unrolling the sheath onto and along the length of the endoscope. When channels have been integrated into the sheath itself, it can be installed by placing the distal end of the endoscope into the proximal end of the sheath (through a close-tolerance seal) and then forcing a gas into the interior of the sheath. The expanded sheath then slides onto the endoscope until the distal end of the endoscope contacts the distal end of the sheath, at which point the flow of gas into the sheath is terminated and the pressure released, thereby allowing the sheath to contract onto the cylindrical wall of the endoscope. The facilitate the introduction of a gas into the interior of the sheath, an inflation nozzle may be mounted on the sheath near its proximal end. A sealing collar may also be provided at the proximal end of the sheath, with the inflation nozzle being positioned between the sealing collar and the distal end of the sheath. The sealing collar reduces the flow of gas from the inside of the sheath when the sheath is being expanded for insertion onto the endoscope.

BRIEF DESCRIPTION OF THE DRAWINGS

FIG. 1 is an isometric view of one type of endoscope illustrating the inventive, protective sheath being installed utilizing one installation technique.

FIG. 2 is an isometric view showing the distal end of the endoscope and protective sheath of FIG. 1 in greater detail.

FIG. 3 is a cross-sectional view taken along the line 3—3 of FIG. 1 showing the protective sheath installed on an endoscope having an externally accessible, longitudinal groove receiving an internal biopsy channel formed in the sheath.

FIG. 4 is a schematic showing the water, suction and air connections to the endoscope and installed protective sheath.

FIG. 5 is an isometric view of another embodiment of the protective sheath before being installed on an endoscope.

FIG. 6 is a cross-sectional view taken along the line 6—6 of FIG. 5.

FIG. 7 is an isometric view showing a protective sheath installed on a conventional endoscope.

FIG. 8 is a cross-sectional view taken along the line 8—8 of FIG. 7.

FIG. 9 is an isometric view of the distal end of a side-looking endoscope.

FIG. 10 is an isometric view of a protective sheath specially adapted for and installed on the sidelooking endoscope of FIG. 9.

FIG. 11 is a side elevational view showing a protective sheath being installed on the side-looking endoscope of FIG. 9, in which a longitudinal groove receives a biopsy channel tube prior to unrolling a covering sheath.

BEST MODE FOR CARRYING OUT THE INVENTION

As illustrated in FIG. 1, an endoscope 8 adapted for use with the inventive protective sheath includes a flexible core 12 extending from a headpiece 14. As is well known in the art, the core 12 includes means for conveying an image from the distal end of the core to the headpiece. A number of devices can be used to perform this function. For example, the distal end of the core may contain a lens that is optically coupled to the headpiece 14 through an optical wave guide, such as a fiber-optic bundle. The distal end of the core 12 may also include a miniature TV camera or other imaging device that is electrically coupled to a monitor either on the headpiece 14 or elsewhere through electrical wires extending through the core 12. Regardless of the structure used, the core 12 will have an optically transparent window at or near its distal end for viewing an image and some structure for optically or electrically coupling this image to at least the headpiece 14.

The endoscope core 12 will also normally include a structure for illuminating tissues to be viewed. These structures can take the form of, for example, a fiber-optic bundle connected to a light source (not shown) and coupled to the headpiece 14 via a fiber-optic bundle (not shown), or the light can be placed directly at the distal end of the core 12, with the light being powered through wires extending from the headpiece 14 through the core 12. In either case, light must be directed from the distal end of the core 12 to the tissues that are to be imaged. The core will also contain the wires which permit bending of the endoscope tip.

Although not required for imaging internal body tissues, endoscopes will also usually have auxiliary tubes or channels extending from the headpieces 14 to the distal end of the core 12 for peforming a variety of functions. One of these tubes is a wash channel by which pressurized water can be injected through a nozzle at the distal end of the core 12 onto a lens covering the distal end of the endoscope core 12 in order to clean the lens of body tissues and fluids. Another channel is used to instill air or $CO_2$ gas to distend the hollow organ and permit visual inspection. A tube extending the length of the endoscope core 12 may also be used to extract fluids or to inject fluids into the body. Finally, various biopsy and other devices, both diagnostic and therapeutic, may be inserted through tubes to perform a specific function at the distal end of the core 12. In any case, conventional endoscopes often employ tubes or channels extending from the headpiece 14 to the distal end of the core 12 for performing the above-noted functions.

The usefulness of conventional endoscopes depends, to a large extent, on the ability to manipulate the position of the distal end of the core 12 when the core 12 is inserted into the body. Manipulation of the core is normally accomplished by retracting and extending control cables symmetrically positioned within the core 12. The control cables are anchored near the distal end of the core 12 and they extend along the length of the core 12 to knobs 15 that are rotated to move the distal end of the core 12 in opposite directions in two orthogonal axes. A pair of trumpet values actuated by respective knobs 16 regulate fluid flow through air and water channels as discussed in greater detail below.

Conventional endoscopes have wash channels, air channels, biopsy channels, suction channels, or injection channels and may not be adequately cleaned even after a great deal of effort. An endoscope can be sterilized with ethylene oxide gas, but there are several drawbacks to this approach: it takes 24 hours; the gas is toxic and must be carefully removed; and the procedure may, after repeated sterilizations, damage the plastic of the endoscope. Gluteraldehyde solutions may be used to soak the endoscope, but this may require more than one hour and may not totally sterilize the endoscope; and, since gluteraldehyde is toxic, the endoscope must be rinsed carefully. The solution can also irritate the person cleaning the endoscope. This difficulty with cleaning endoscopes exists rpincipally because the internal channels extending through the core 12 are not readily accessible to cleaning instruments or fluids. Isolation of the endoscope from the patient thus requires that any component coming into contact with a patient, including externally accessible channels, be removable and, preferably, disposable.

One embodiment of a protective endoscope sheath 10 for isolating the endoscope from a patient is illustrated in FIGS. 1–3. As best illustrated in FIG. 3, the core 12 of the endoscope is basically circular, as in conventional designs, except that it contains a U-shaped cutout 21. As explained in greater detail below, the cutout 21 accommodates one or more biopsy channels, an air channel and a wash channel. The U-shaped configuration of the groove, while not essential, is preferable because it allows for equidistant control cable placement. This provides symmetrical control on both axes. However, other shapes are also feasible and would include (not shown): multiple cutouts (for multiple channels), circle sections, D-shaped sections and a rectangular cross section.

With reference also, now, to FIGS. 1 and 2, the protective sheath includes a cylindrical end cap 30 having a viewing window 32 mounted at one end. The viewing window 32 is basically circular, but it, like the core 12, contains a U-shaped cutout 34. As best illustrated in FIG. 3, a tube system 35 having a cylindrical biopsy channel 36, a water channel 38 and an air channel 39 extends through the U-shaped cutout 21 of the core 12. The tube system 35 is inserted in the U-shaped cutout 21 of the endoscope core 12 for substantially its entire length, as illustrated in FIG. 1. The biopsy channel 36 and air channel 39 extend through the window 32 and are sealed thereto to isolate the inside of the window 32 from the external environment. The water channel 38 terminates in a fluid tube 40 integrally formed in the window 32. The fluid tube, in turn, terminates in a spray nozzle 42 projecting from the outer surface of the window 32. As explained in greater detail below, pressurized water flowing through the channel 38 sprays out the nozzle 42 onto the window 32 to clean the window 32 of body fluids and tissues. The window 32 also includes a window portion 44 through which light emitted from the core 12 passes to illuminate body tissues. An optical barrier or baffle 46 prevents light emitted from a source in the core 12 from reflecting across the internal surfaces of the window 32 and adding glare to the image seen by the viewing lens. Antireflection coatings can be used on both optical windows 32 and illumination window portion 44 to improve optical efficiency.

In use, the cylindrical support body 30 is placed on the distal end of the endoscope core 12, with the biopsy channel tube system 35 received in the U-shaped groove 21 in the core 12. The remainder of the biopsy channel tube system 35 is then inserted in the groove 21, and a roll of elastomeric material 48 that is secured to the support body 30 is unrolled over the endoscope core 12. When the elastomeric material 48 has been completely unrolled, its proximal end extends to the headpiece 14, thereby completely isolating the endoscope 12 from the patient. Moreover, all externally accessible surfaces, such as the biopsy channel lumen 36, water channel lumen 39 and air channel lumen 39, are part of the removable protective sheath and are totally isolated from the endoscope. As a result, after an endoscopy has been performed, the sheath 10 may be removed from the endoscope, leaving the endoscope sterilized (if it was sterilized beforehand) without the need for expensive and time-consuming washing. It will also be apparent that if the endoscope was not sterile before the protective sheath was applied, the protective sheath also isolates the patient from the nonsterile endoscope. In other words, the sheath keeps the endoscope surfaces clean during a procedure. When the sheath and channel systems are removed and disposed of after the procedure, the endoscope should remain clean. A backup assurance occurs when a new sterile sheath is placed prior to the next patient's examination to protect that patient in case sme contaimination of the endoscope surface did occur during the prior procedure.

The connections of external equipment to the channels of the protective sheath are illustrated in FIG. 4. The water channel 38 is connected to a conventional source of high-pressure water through a conventional valve 50. Similarly, the air channel 39 can be connected to a source of pressurized gas through a valve 52. Finally, the biopsy channel 36 can be used, as illustrated in FIG. 4, for suction by connecting the channel 36 to a conventional suction device through a valve 54. Orifice 55 allows insertion of biopsy and other diagnostic (cytology) and therapeutic devices (laser wave guides, etc.) for delivery to the distal orifice 36.

An alternative embodiment of the endoscope is illustrated in FIGS. 5 and 6. Because the elastomeric material 48 must fit snugly around the endoscope core 12, the variety of procedures for installing the sheath on the endoscope are limited. It is not possible to simply pull on the tight sheath over the endoscope, partly because of the endoscope length, which may be as long as two meters. One technique for installing the sheath on an endoscope is illustrated in FIG. 1. In the technique illustrated in FIG. 1, the elastomeric material 48 is rolled into an annular configuration and then unrolled along the core 12. If the biopsy channel 36 and other channels (38 and 39) are integrated with the sheath 48 (as shown in FIG. 6), it is impossible to roll the composite. To circumvent this problem, another installation method was devised. In the embodiment illustrated in FIG. 5, the proximal end of the elastomeric material 48 terminates in an inflation collar 60 which may consist of a cylindrical body 62, an inflation nozzle 64, an annular seal 66 (FIG. 6), and a seat 68 to which the distal end of the elastomeric material 48 is attached. In operation, the annular seal 66 is placed over the distal end of the endoscope core 12. A source of pressurized gas is then applied to the inflation nozzle 64, thereby causing the elastomeric material 48 to expand. Since the diameter of the elastomeric material 48 is now substantially larger than the diameter of the endoscope core 12, the elastomeric material 48 easily slips on to the core 12, with the seal 66 sliding along the endoscope core 12. After the protective sheath has been fully installed on the endoscope with the distal end of the endoscope abutting the viewing window 32, the source of pressurized gas is removed from the inflation nozzle 64 and the sheath collapses to a tight fit on the endoscope. The instrument is then ready for use and the endoscopy is performed. Upon completion of the endoscopy, pressurized gas is once again applied to the inflation nozzle 64, thereby expanding the elastomeric material 48 and allowing it to be easily slipped off the endoscope core 12.

It has been noted that the endoscope 8, used with the endoscope sheath 10 in the embodiment of FIGS. 1–6, has a longitudinal groove 21 that is specially adapted to receive the biopsy channel tube system 35. Of course, conventional endoscopes do not have this longitudinal channel.

A simple form of an embodiment usable with conventional endoscopes is illustrated in FIGS. 7 and 8. In this embodiment, the endoscope core is surrounded by an elastomeric cylinder 70 terminating in an end cap 72. The entire distal end of the end cap 72 is covered with a transparent window 74 which the distal end of the endoscope core abuts. Integrally formed with the elastomeric sheath 70 and the end cap 72 is a biopsy channel 76 that has an open distal end 78. The end cap 72 thus surrounds the distal end of the endoscope and biopsy channel 78. It will be understood, however, that the biopsy channel 76 can incorporate additional channels, as with the embodiments of FIGS. 1–6. For example, a washing nozzle may be used to wash body fluids and tissues from the external surface of the window 74. Finally, although the biopsy channel 76 in the embodiment of FIGS. 7–8 extends along the ouside wall of the sheath 70, it will be understood that the channel 76 may also extend along the inside wall of the sheath 70. In either case, this retrofit system would require the gas flotation installation system illustrated in FIGS. 5 and 6.

The principal disadvantage of the embodiment in FIGS. 7 and 8 is that the protective sheath increases the transverse dimension of the endoscope. However, the embodiments of FIGS. 7 and 8 do allow conventional endoscopes to be used in a manner that prevents patient contamination without time-consuming, expensive and unsatisfactory washing. Since several sheath configurations are possible, all fitting over the same core endoscope, this system allows the endoscopist to use one core endoscope and yet have a family of different endoscopes as various specific sheaths are used. Furthermore, since multiple channel configurations can be considered with a sheath designed for a specific purpose, new technologies may be possible via the endoscope, such as multiple electrical wires to activate an ultrasound device or hydraulic channels to activate a hydraulic device.

In order to allow the endoscope sheath to be retrofitted with existing endoscopes without increasing the transverse dimensions of the endoscope, the sheath may be designed so that the tube system of the sheath can be inserted through the distal end of the endoscope biopsy channel.

As alluded to in the previous paragraph, the protective sheath allows a multitude of special purpose endoscopes to be quickly and inexpensively created. The most expensive portion of an endoscope is the core, which contains expensive optical coomponents. A variety of special purpose protective sheaths may be installed on a single, relatively expensive endoscope for use in performing a variety of specialized procedures. The function performed by the endoscope depends upon the type of medical instrument mounted at the end of the biopsy channel 36. Thus, for example, hydraulically actuated scissors, clamps, grasping tools or balloons may be attached to the end of the biopsy channel and operated by fluid pressure applied to the proximal end of the biopsy channel. Electrical devices, such as electrocoagulation units, hyperthermia devices, ultrasound transducers and a variety of electrical sensors may be attached to the distal end of the biopsy channel and operated through wires extending through the biopsy channel. Mechanical devices, such as grasping devices and cutting devices, may also be attached to the distal end of the biopsy channel and operated by a mechanical actuating member, such as an actuating cable or flexible drive shaft. Optical devices, such as laser Doppler flowmeters, illuminating devices, imaging devices, diaphenography devices, photocoagulation units, etc., may be connected to a fiber-optic wave guide extending through the biopsy channel.

As mentioned above, the inventive endoscope sheath may also be used with side-looking endoscopes. As illustrated in FIG. 9, side-viewing endoscopes 90 include a cylindrical endoscope core 92 terminating in a fiber bundle cap 94 having a viewing window 96 and a light source 98 on an axial face. As is well known in the art, light is emitted from the light source 98 to allow tissues to be viewed through the window 96. The end of the catheter is longitudinally deflected by an elevator 100 containing an arcuate surface 102 that engages the catheter. The elevator 100 is pivotally mounted at 104 and it is manipulated by drawing in or extending an elevator pull cable 106 from the headpiece. By pivoting the elevator 100 through the pull cable 106, the physician can manipulate the end of the catheter in front of the window 96 in a plane perpendicular to the viewing window 96 and parallel to the axis of the endoscope core 92.

Where the endoscope 90 illustrated in FIG. 9 departs from conventional endoscopes is in the use of a longitudinal groove 108 extending along the length of the endoscope core 92. As explained in greater detail below, the slot 108 receives a tube system in a similar manner to the tube system 35 inserted in the longitudinal slot 21 in the end-viewing endoscope, illustrated in FIGS. 1-3.

The protective sheath for side-viewing endoscopes is illustrated in FIGS. 9 and 10, with the sheath installed on the endoscope. The sheath 110 includes an end cap 112 of relatively rigid material mounted at the end of a flexible cylindrical tube of elastomeric material 114 formed into a roll 116, as illustrated in FIG. 10. A removable cover 113 protects the end cap 112 and supports the roll 116 during shipment. The end cap 112 includes a pair of transparent windows 118, 120 positioned over the viewing window 96 and the light source 98, respectively, of the endoscope (FIG. 9). Light emitted by the endoscope through window 98 shines through window 120 to illuminate internal body tissues. These tissues are then viewed through the window 118 of the end cap 112 and through window 96 of the endoscope. A wash port 121 is connected to a wash tube in a manner similar to wash port 42 and wash tube 38 of the embodiment of FIGS. 1-6 to maintain window 118 free of substances that would otherwise obscure the window 118.

It will be recalled that manipulation the elevator pull cable 106 causes the elevator 100 to pivot, thereby moving the end of a catheter axially in front of the window 96. The inventive endoscope sheath utilizes a tube system 130 bonded to the end cap 112. The biopsy channel portion extends past the previously mentioned anchor point, as explained in greater detail below. This biopsy channel terminates in biopsy channel port 122 formed in a highly elastic membrane 124. The membrane 124 is mounted in a rectangular slot in the end cap 112. Consequently, pivotal movement of the elevator 100 moves the biopsy channel, and consequently the biopsy channel port 122, longitudinally.

The protective sheath for side-looking endoscopes is preferably installed as illustrated in FIG. 11. A tube system 130 has a biopsy channel that extends from the biopsy channel port 122 inside the end cap 112. The end cap 112 is first inserted onto the end of the endoscope, with the channel tube 130 being drawn to the right, as illustrated in FIG. 11, so that it passes along the curved surface 102 of the elevator 100. After the sheath 112 has assumed the position illustrated in FIG. 10, the tube system 130 is inserted in the longitudinal groove 108 along the entire length of the endoscope core 92. The tube of elastomeric material 114 is then unrolled from the roll 116 along the length of the endoscope core 92. The protective cover 113 is then romoved, thereby completing the installation. The endoscope is then inserted into the patient, allowing the physician to view through the window 96 and manipulate a catheter inserted through the biopsy channel 130 by actuating the cable 106. During this time, the endoscope 90 is totally isolated from the patient. After use, the tube of elastomeric material 114 is rolled downward along the endoscope core 92, the biopsy channel tube 130 is removed from the groove 108, and the end cap 112 is then removed from the endoscope fiber bundle cap 94.

Although the embodiment shown in FIGS. 9-11 utilizes an elevator for a side-viewing endoscope, it will be understood that the protective sheath may also be adapted for use with an end-viewing endoscope having an elevator. The elevator is used to radially displace a catheter extending through the biopsy channel in the field of view of the endoscope.

Returning now to FIG. 1, in order to more completely isolate the endoscope 8 from the external environment, an elastomeric isolation bag 140 may be inserted over the headpiece 14 and over the proximal end of the elastomeric tube 48. The isolation bag 140, by surrounding the endoscope controls and valves in the headpiece 14, prevents even the headpiece 14 from directly or indirectly making contact with the patient. This end cover can also be made such that a control shaft extends through the bag and a set of sterile control handles are installed. This method would allow more freedom of movement than the bag method alone.

We claim:

1. An endoscope sheath comprising a flexbile, elongated, thin-walled tube adapted to fit over and tightly surround an elongated, flexible endoscope to isolate at least a portion of said endoscope from said external environment, said sheath having an opening at its proximal end for receiving the distal end of an endoscope and a window near its distal end adapted to be positioned over the viewing window of an endoscope, said sheath further including a channel extending from a channel port along the length of said tube, said channel port being positioned near the window of said sheath.

2. The endoscope sheath of claim 1 wherein the window of said sheath faces in an axial direction so that said sheath can be used with end-looking endoscopes having an axially facing window.

3. The endoscope sheath of claim 1 wherein the window of said sheath faces in a radial direction so that said sheath can be used with side-looking endoscopes having a radially facing window.

4. An endoscope sheath comprising a flexible, elongated, thin-walled tube adapted to fit over and tightly surround a side-looking elongated, flexible endoscope to isolate at least a portion of said endoscope from said external environment, said sheath having an opening at its proximal end for receiving the distal end of an endoscope and a radially facing window near its distal end adapted to be positioned over the radially facing viewing window of a side-looking endoscope, said endoscope sheath further including a channel extending from a channel port along the length of said tube, said channel port being positioned near the window of said sheath.

5. The endoscope sheath of claim 4 wherein the distal end of said tube terminates in a end cap having a sidewall extending toward the proximal end of said tube, said sidewall having mounted therein the viewing window of said sheath and an elastomeric member having an elongated configuration extending along the longitudinal axis of said tube, said channel port being formed in said elastomeric member so that a biopsy catheter may be inserted through said channel with the distal end of said catheter projecting from said channel port and being moved longitudinally in said end cap.

6. An endoscope sheath comprising a flexible, elongated, thin-walled tube adapted to fit over and tightly surround an elongated, flexible endoscope to isolate at least a portion of said endoscope from said external environment, said sheath having an opening at its proximal end for receiving the distal end of an endoscope and a window near its distal end adapted to be positioned over the viewing window of an endoscope, said sheath further including a channel extending along the length of said sheath, said channel having open distal and proximal ends so that the interior of said channel is externally accessible but isolated from the interior of said sheath.

7. The endoscope sheath of claim 6 wherein said channel is positioned within the interior of said sheath with the distal end of said channel extending through the distal end of said sheath.

8. An endoscope sheath comprising a flexible, elongated, thin-walled tube adapted to fit over and tightly surround an elongated, flexible endoscope to isolate at least a portion of said endoscope from said external environment, said sheath having an opening at its proximal end for receiving the distal end of an endoscope and a window near its distal end adapted to be positioned over the viewing window of an endoscope, said sheath further including an inflation nozzle near the proximal end of said sheath, said nozzle communicating with the interior of said sheath to allow said sheath to be inflated to facilitate insertion of an endoscope into said sheath.

9. The endoscope sheath of claim 8, further including a sealing collar at the proximal end of said sheath, with said inflation nozzle being positioned between said sealing collar and the distal end of said sheath, said sealing collar being adapted to reduce the flow of gas from inside said sheath when an endoscope is being inserted into said sheath through said sealing collar and the gas is being forced into said inflation nozzle.

10. An endoscope sheath comprising a flexible, elongated, thin-walled tube adapted to fit over and tightly surround an elongated, flexible endoscope to isolate at least a portion of said endoscope from said external environment, said sheath having an opening at its proximal end for receiving the distal end of an endoscope and a window near its distal end adapted to be positioned over the viewing window of an endoscope, said sheath further including a channel extending along the length of said sheath within its interior, said channel having open distal and proximal ends, with the distal end extending through the window at the distal end of said sheath so that the interior of channel is externally accessible.

11. An endoscope sheath comprising a flexible, elongated, thin-walled tube adapted to fit over and tightly surround an elongated, flexible endoscope to isolate at least a portion of said endoscope from said external environment, said sheath having an opening at its proximal end for receiving the distal end of an endoscope and a window near its distal end adapted to be positioned over the viewing window of an endoscope, said sheath further including a channel extending along said sheath and a washing nozzle mounted in the distal end of said channel, said nozzle being aimed at the outer surface of the window at the distal end of said sheath.

12. The endoscope sheath of claim 11, further including a second channel extending along the length of said sheath, said second channel having open distal and proximal ends, with the distal end extending through the window at the distal end of said sheath so that the interior of said second channel is externally accessible.

13. An endoscope sheath comprising a flexible, elongated, thin-walled tube adapted to fit over and tightly surround an elongated, flexible endoscope to isolate at least a portion of said endoscope from said external environment, said sheath having an opening at its proximal end for receiving the distal end of an endoscope and a window near its distal end adapted to be positioned over the viewing window of an endoscope, said sheath further including a relatively rigid, cylindrical support body in which said window is mounted, said support body being mounted at the distal end of said sheath so that said window is connected to said sheath through said support body.

14. The endoscope sheath of claim 13 wherein the plane of said window is perpendicular to the axis of said cylindrical support body and said cylindrical support body is coaxial with such sheath.

15. An endoscope sheath comprising a flexible, elongated, thin-walled tube adapted to fit over and tightly surround an elongated, flexible endoscope to isolate at least a portion of said endoscope from said external environment, said sheath having an opening at its proximal end for receiving the distal end of an endoscope and a window near its distal end adapted to be positioned over the viewing window of an endoscope, said sheath further including a channel extending along the length of said tube, said channel having an open proximal end and a distal end communicating with a specialized medical instrument whereby a variety of said endoscope sheaths may be used with a relatively expensive endoscope to create a variety of specialized endoscopes.

16. The endoscope sheath of claim 15 wherein said instrument is hydraulically actuated so that it may be operated by fluid pressure applied through said channel.

17. The endoscope sheath of claim 15 wherein said instrument is mechanically actuated so that it may be operated by a mechanical actuating member extending through said channel.

18. The endoscope sheath of claim 15 wherein said instrument is electrically operated so that it may be operated through wires extending through said channel.

19. The endoscope sheath of claim 15 wherein said instrument is an optical device that may be connected to an optical wave guide extending through said channel.

20. An endoscope having a removable protective sheath, comprising:

an elongate, flexible endoscope having a viewing window at its distal end and means for conveying an image viewed through said window to the proximal end of said endoscope; and a thin-walled, flexible, elongated sheath fitting over and tightly surrounding said endoscope to isolate at least a portion of said endoscope from the external environment, said sheath having a window near its distal end positioned over the viewing window of said endoscope and an opening at its proximal end from which the proximal end of said endoscope projects, said sheath further including a channel extending along the length of said sheath to the distal end thereof, said channel having open distal and proximal ends so that the interior of said channel is externally accessible and isolated from the interior of said sheath.

21. The endoscope of claim 20 wherein said channel is positioned within the interior of said sheath with the distal end of said channel extending through the distal end of said sheath.

22. An endoscope having a removable protective sheath, comprising:

an elongated, flexible endoscope having a viewing window at its distal end and means for conveying an image viewed through said window to the proximal end of said endoscope; and a thin-walled, flexible, elongated sheath fitting over and tightly surrounding said endoscope to isolate at least a portion of said endoscope from the external environment, said sheath having a window near its distal end positioned over the viewing window of said endoscope and an opening at its proximal end from which the proximal end of said endoscope projects, said sheath further including an inflation nozzle near the proximal end of said sheath, said nozzle communicating with the interior of said sheath to allow said sheath to be inflated to facilitate insertion of an endoscope into said sheath.

23. The endoscope of claim 22, further including a sealing collar at the proximal end of said sheath, with said inflation nozzle being positioned between said sealing collar and the distal end of said sheath, said sealing collar having a circular seal extending around said endoscope to reduce the flow of gas from inside said sheath when said endoscope is inserted into said sheath through said sealing collar and a gas is being forced into said inflation nozzle.

24. An endoscope having a removable protective sheath, comprising:

an elongated, flexible endoscope having a viewing window at its distal end and means for conveying an image viewed through said window to the proximal end of said endoscope; and a thin-walled, flexible, elongated sheath fitting over and tightly surrounding said endoscope to isolate at least a portion of said endoscope from the external environment, said sheath having a window near its distal end positioned over the viewing window of said endoscope and an opening at its proximal end from which the proximal end of said endoscope projects, said sheath further including a channel extending along said sheath and a washing nozzle mounted in the distal end of said channel, said nozzle being aimed at the outer surface of the window at the distal end of said sheath.

25. An endoscope having a removable protective sheath, comprising:

an elongated, flexible endoscope having a viewing window at its distal end and means for conveying an image viewed through said window to the proximal end of said endoscope; and a thin-walled, flexible, elongated sheath fitting over and tightly surrounding said endoscope to isolate at least a portion of said endoscope from the external environment, said sheath having a window near its distal end positioned over the viewing window of said endoscope and an opening at its proximal end from which the proximal end of said endoscope projects, said sheath further including a relatively rigid support body in which said window is mounted, said support body being mounted at the distal end of said sheath in coaxial relationship with said endoscope.

26. An endoscope having a removable protective sheath, comprising:

an elongated, flexible endoscope having a viewing window at its distal end and means for conveying an image viewed through said window to the proximal end of said endoscope, said endoscope further including endoscope controls and valves at its proximal end; and a thin-walled, flexible, elongated sheath fitting over and tightly surrounding said endoscope to isolate at least a portion of said endoscope from the external environment, said sheath having a window near its distal end positioned over the viewing window of said endoscope and an opening at its proximal end from which the proximal end of said endoscope projects, said sheath further including an isolation bag sealingly engaging said endoscope sheath, said isolation bag surrounding said endoscope controls and valves to substantially isolate the proximal end of said endoscope from the external environment.

27. An endoscope comprising an elongated core having a viewing window at its distal end and an optical viewing system allowing objects positioned in front of said viewing window to be viewed from the proximal end of said endoscope, said core having formed therein an externally accessible, longitudinal groove whereby a protective sheath having an internal longitudinal channel may be placed over said endoscope.

28. The endoscope of claim 27 wherein said viewing window faces in a direction extending along the longitudinal axis of said endoscope to provide end-viewing capability.

29. The endoscope of claim 27 wherein said viewing window faces in a direction extending perpendicular to the longitudinal axis of said endoscope to provide side-viewing capability.

30. A method of isolating a flexible endoscope from viruses, bacteria and the like in an external environment, said endoscope having formed therein a longitudinal groove, said method comprising the step of placing a thin-walled, flexible, elongated sheath over said endoscope, said sheath having an opening at its proximal end through which the proximal end of said endoscope is adapted to extend and a window at its distal end positioned over the viewing window of an endoscope, and a channel extending along the length of said sheath within its interior with its distal end extending through the distal end of said sheath, said sheath being installed on said endoscope by rolling up said sheath from its proximal end toward its distal end, placing the distal end of said sheath adjacent the distal end of said endoscope, placing the channel of said sheath in the groove of said endoscope, and then unrolling said sheath onto and along the length of said endoscope.

31. A method of isolating a flexible endoscope from viruses, bacteria and the like in an external environment, said method comprising the step of placing a thin-walled, flexible, resilient, elongated sheath over said endoscope, said sheath having an opening at its proximal end through which the proximal end of said endoscope extends and a window at its distal end positioned over the viewing window of an endoscope, said sheath being resilient and is installed on said endoscope by placing the distal end of said endoscope into the proximal end of said sheath, forcing a gas into the interior of said sheath to expand the walls of said sheath, then sliding said sheath onto said endoscope, and, when said sheath has been installed on said endoscope, terminating the flow of gas into the interior of said sheath to allow said sheath to contract onto the cylindrical wall of said endoscope.

* * * * *

UNITED STATES PATENT AND TRADEMARK OFFICE
CERTIFICATE OF CORRECTION

PATENT NO. : 4,646,722

DATED : Mar. 3, 1987

INVENTOR(S) : Fred E. Silverstein, Eric A. Opie

It is certified that error appears in the above—identified patent and that said Letters Patent is hereby corrected as shown below:

1) Col. 13, line 1
change "elongate" to --elongated--

Col. 14, line 55
change "havingformed" to --having formed--

Signed and Sealed this

Eighth Day of September, 1987

Attest:

DONALD J. QUIGG

Attesting Officer

Commissioner of Patents and Trademarks